(12) United States Patent
Lu et al.

(10) Patent No.: US 10,113,933 B2
(45) Date of Patent: Oct. 30, 2018

(54) LEAKAGE OIL DETECTOR SYSTEM AND METHOD

(71) Applicant: HITACHI, LTD., Tokyo (JP)

(72) Inventors: Li Lu, Tokyo (JP); Toshiaki Rokunohe, Tokyo (JP); Tomohiro Moriyama, Tokyo (JP); Jun Nukaga, Tokyo (JP); Akira Yamagishi, Tokyo (JP); Yasutomo Saito, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/519,301

(22) PCT Filed: Mar. 27, 2015

(86) PCT No.: PCT/JP2015/059542
§ 371 (c)(1),
(2) Date: Apr. 14, 2017

(87) PCT Pub. No.: WO2016/059812
PCT Pub. Date: Apr. 21, 2016

(65) Prior Publication Data
US 2017/0234762 A1    Aug. 17, 2017

(30) Foreign Application Priority Data
Oct. 17, 2014  (JP) ................. 2014-212189

(51) Int. Cl.
*G01M 3/38* (2006.01)
*G01N 21/64* (2006.01)
(Continued)

(52) U.S. Cl.
CPC .......... *G01M 3/38* (2013.01); *G01N 21/6456* (2013.01); *G01N 33/28* (2013.01); *H01F 27/12* (2013.01);
(Continued)

(58) Field of Classification Search
CPC ..... G01M 3/38; G01N 21/6456; G01N 33/28; H01F 27/12
See application file for complete search history.

(56) References Cited

U.S. PATENT DOCUMENTS 5,281,826 A    1/1994  Ivancic et al.
5,974,860 A   11/1999  Kuroda et al.
(Continued)

FOREIGN PATENT DOCUMENTS

JP    1995-503317 A    4/1995
JP    1996-128916      5/1996
(Continued)

OTHER PUBLICATIONS

International Search Report for WO 2016/059812 A1, dated Jun. 16, 2017.

*Primary Examiner* — Mark R Gaworecki
(74) *Attorney, Agent, or Firm* — Volpe and Koenig, P.C.

(57) ABSTRACT

A system and method for detecting leakage oil with a high degree of accuracy while avoiding the complexity of the system and the influence of noise light comprise: ultraviolet light sources arranged to irradiate an oil-filled device from a plurality of different incidence angles, and are switched on and off at the respective incidence angles in sequence, and include a wavelength exciting oil; an imaging device to photograph the oil-filled device irradiated with ultraviolet light emitted from the ultraviolet light sources when the ultraviolet light sources are switched on; a recorder to record respective images photographed by the imaging device; and a display to display the respective images. The respective images are compared, a site where a light emitting position does not change always is judged as a leakage oil site, and a site emitting light or not emitting light occasionally is judged as a noise light site.

9 Claims, 15 Drawing Sheets

(51) Int. Cl.
*G01N 33/28* (2006.01)
*H01F 27/12* (2006.01)

(52) U.S. Cl.
CPC ... *G01N 2021/6465* (2013.01); *H05K 999/99* (2013.01)

(56) References Cited

U.S. PATENT DOCUMENTS

| | | | |
|---|---|---|---|
| 2012/0062871 A1* | 3/2012 | Bugge | G01N 33/1833 356/51 |
| 2012/0140233 A1* | 6/2012 | Rockwell | G01N 21/55 356/445 |
| 2015/0192466 A1* | 7/2015 | Kusukame | G01N 21/35 250/338.4 |
| 2016/0266247 A1* | 9/2016 | Hjelmstad | G01S 17/102 |
| 2016/0275699 A1* | 9/2016 | Lu | G06T 7/408 |

FOREIGN PATENT DOCUMENTS

| | | | |
|---|---|---|---|
| JP | 1997-304281 A | 11/1997 | |
| JP | 5351081 B2 | 11/2013 | |

* cited by examiner

LEAKAGE OIL DETECTOR SYSTEM AND METHOD

TECHNICAL FIELD

The present invention relates to a method and a system for detecting leakage oil in an oil-filled device such as a transformer, a condenser, a hydraulic operating unit of a GIS, or a rectifier.

BACKGROUND ART

There has heretofore been concern that oil leakage (leakage oil) may be caused by deterioration, an accident, or the like in an oil storage tank, a transformer, or the like. The leakage oil may possibly lead to environmental pollution and a disaster and hence a technology of detecting a tiny amount of leakage oil at the initial stage of deterioration has been desired. As a prior art for detecting a tiny amount of leakage oil, there is a technology of detecting fluorescence (self-luminescence) emitted from a leakage oil when ultraviolet light including an absorption wavelength of the leakage oil is applied from an exterior.

Black light is generally used as an external irradiation light source of such ultraviolet light but the irradiation light of the black light may sometimes include a visible light component having a wavelength close to the ultraviolet light in addition to the ultraviolet light. As a result, there is the concern that strongly reflected light (noise light) in a visible light component included in the light source is also detected together with a fluorescence and hinders the detection and thus the improvement of the accuracy of detection and diagnosis by the removal of noises has been needed.

As a prior art for solving the problem, as described in Japanese Patent Application Laid-Open No. H09-304281 (Patent Literature 1), there is a method of improving detection accuracy by: irradiating a leakage oil with a pulsed laser; and observing only fluorescence with a wavelength selection element using a band-pass filter and an image intensifier having a high-speed shutter function to detect only the fluorescence and an image multiplication function.

CITATION LIST

Patent Literature

PTL 1: Japanese Patent Application Laid-Open No. H09-304281

SUMMARY OF INVENTION

Technical Problem

The problems of the technology described in Patent Literature 1, however, have been: the concern that the structure of a detector is increasingly complicated; the necessity of changing a band-pass filter for each of oil types; and others. Further, because of a sensitive device, time and effort have been required for the maintenance of the device and others when the device is installed all the time in a field.

Solution to Problem

In order to solve the above problems, a leakage oil detector system according to the present invention is characterized by having: an ultraviolet light source that is arranged so as to irradiate an oil-filled device from a plurality of different incidence angles, is switched on and off at the respective incidence angles in sequence, and includes a wavelength exciting oil; an imaging device to photograph the oil-filled device irradiated with ultraviolet light emitted from the ultraviolet light source when the ultraviolet light source is switched on; a recorder to record respective images photographed by the imaging device; and a display to display the respective images in order to compare the respective images, judge a site where a light emitting position does not change always as a leakage oil site, and judge a site emitting light or not emitting light occasionally as a noise light site.

Advantageous Effects of Invention

The present invention makes it possible to materialize a method and a system for detecting leakage oil with a high degree of detection accuracy while avoiding the complexity of the system and the influence of noise light.

DESCRIPTION OF EMBODIMENTS

Embodiments of a method and a system for detecting leakage oil according to the present invention are explained hereunder in reference to FIGS. 1 to 17. Here, the embodiments described in the present description do not limit the present invention. Although a method and a system for detecting leakage oil are explained in the following embodiments with an insulation oil (mineral oil, vegetable ester oil, or the like) used generally in a transformer used as an example, the present invention is widely applicable also to a method and a system for detecting leakage oil in a general oil-filled device and is not limited to a transformer. For example, the present invention is applicable also to the detection of leakage oil in a tank reserving a fuel oil, a pipeline, or the like.

First Embodiment

Figure 1:
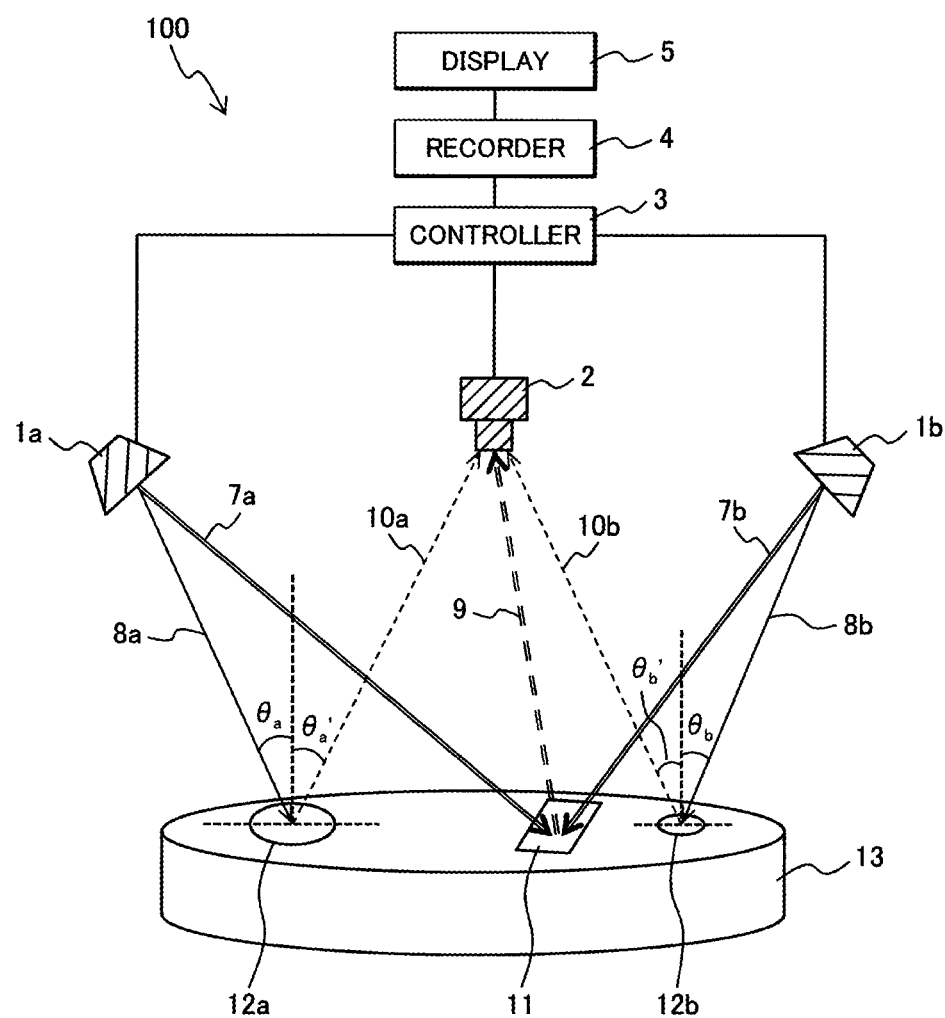
FIG. 1 is a view showing a first embodiment of a leakage oil detector system according to the present invention.

FIG. 1 is a view showing a first embodiment concretely representing a method and a system for detecting leakage oil according to the present invention.

A leakage oil detector system 100 has a first ultraviolet light source 1a, a second ultraviolet light source 1b, an imaging device 2 arranged fixedly, a controller 3 to control the operations of the first ultraviolet light source 1a, the second ultraviolet light source 1b, and the imaging device 2, a recorder 4 to record a photographed image, and a display 5 to display an image stored in the recorder 4.

Here, ultraviolet light sources including an absorption wavelength of oil are used as the first ultraviolet light source 1a and the second ultraviolet light source 1b. Concretely, black light having a light emission peak of 265±50 nm, 275±50 nm, 345±50 nm, or 365±50 nm can be used. Among those, the black light having the light emission peak of 365±50 nm is preferably used in particular.

The imaging device 2 can output image data to an exterior. The imaging device 2 may be a general device such as a digital camera receiving visible light, for example. The first ultraviolet light source 1a and the second ultraviolet light source 1b are arranged preferably with the imaging device 2 interposed in between.

A leakage oil 11 emits a fluorescence 9 when the leakage oil 11 is irradiated with an ultraviolet light component 7a or 7b from the first ultraviolet light source 1a or the second ultraviolet light source 1b. Since the fluorescence 9 is visible light, the fluorescence 9 can be photographed by the imaging device 2 for visible light.

A black light which is an ultraviolet light source generally includes a visible light component in addition to an ultraviolet light component and hence the visible light is reflected on the surface of an imaging object 13. The reflected light is divided into diffuse reflected light and specular reflected light by the surface condition of the imaging object 13. Since the reflected light is visible light, the reflected light can be photographed by the imaging device 2 for visible light.

When only diffuse reflected light is photographed, the intensity of the photographed visible light is generally smaller than the intensity of the fluorescence 9, hence the light emission by the fluorescence 9 appears conspicuously, and the detection of a leakage oil 11 is not hindered. When specular reflected light is generated however, the intensity of the photographed reflected light comes to be comparable with the intensity of the fluorescence 9 sometimes in accordance with the arranged position of the imaging device 2.

For example, when an imaging object 13 is irradiated by the first ultraviolet light source 1a, the intensity of a specular reflected light 10a of a visible light component 8a in the irradiation light of the first ultraviolet light source 1a comes to be the maximum when an incidence angle $\theta_a$ and a reflection angle $\theta_a'$ are equal to each other at a surface site 12a of the imaging object 13. That is, when the imaging device 2 is located in the incident direction of the specular reflected light 10a, visible light of a high intensity is photographed from the surface site 12a of the imaging object 13. The intensity is comparable to the intensity of the fluorescence 9 and a leakage oil is hardly detected disadvantageously. The specular reflected light of a visible light component of an ultraviolet light source photographed into the imaging device 2 is hereunder described as noise light. For example, the specular reflected light 10a is described as noise light 10a.

As explained above, in an image photographed by using the first ultraviolet light source 1a and the imaging device 2, for example, the surface site 12a of the imaging object 13 is the site emitting the noise light 10a.

Likewise, when the imaging object 13 is irradiated by the second ultraviolet light source 1b, a fluorescence 9 emitted by the ultraviolet light component 7b in the irradiation light and noise light 10b is emitted from a surface site 12b of the imaging object 13 by a visible light component 8b. Here, an incidence angle $\theta_b$ and a reflection angle $\theta_b'$ are in the relationship of being equal to each other.

Meanwhile, although only the ultraviolet light components 7a and 7b and the visible light components 8a and 8b causing specular reflection are shown as irradiation light emitted from the ultraviolet light sources 1a and 1b in order to make the explanation easy to understand in FIG. 1, obviously the whole range of the imaging object 13 is irradiated by the ultraviolet light sources 1a and 1b. Other than the fluorescence 9 and the noise light 10a and 10b caused by the specular reflection generated by the ultraviolet light components 7a and 7b and the visible light components 8a and 8b, however, comes to be diffuse reflected light and does not form an emission image of a high intensity in the imaging device 2.

Here, since the imaging device 2 is fixed and the fluorescence 9 is self-luminescence, the emission position of the fluorescence 9 caused by a leakage oil 11 in an image photographed by the imaging device 2 does not change regardless of the arrangement positions of the first ultraviolet light source 1a and the second ultraviolet light source 1b and the irradiation angles to the imaging object 13.

By comparing an image photographed when only the first ultraviolet light source 1a is used for irradiation with an image photographed when only the second ultraviolet light source 1b is used for irradiation therefore, it is possible to detect and identify: a site where light emission is observed always at an identical position in the images (AND condition) as the position of a leakage oil 11; and a site where light emission is observed at different positions in the respective images (OR condition) as a noise light generating position.

The operations of a leakage oil detector system according to the present embodiment are explained in detail hereunder in reference to FIGS. 1, 2, 3, and 4.

Figure 3:
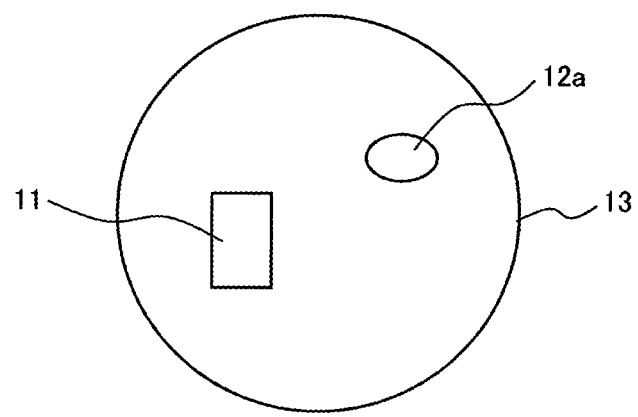
FIG. 3 is a schematic view of an image including a leakage oil and noise light obtained when a first ultraviolet light source is used for irradiation in the first embodiment.
Figure 4:
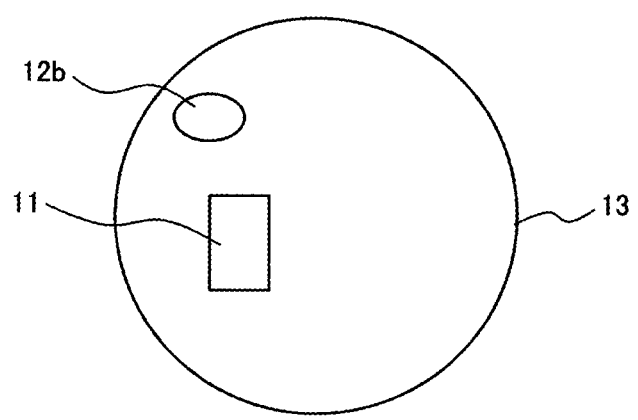
FIG. 4 is a schematic view of an image including a leakage oil and noise light obtained when a second ultraviolet light source is used for irradiation in the first embodiment.

First, at STEP 1, an imaging object 13 is irradiated by a first ultraviolet light source 1a. When the ultraviolet light component 7a of the irradiated light is emitted to a leakage oil 11, the leakage oil 11 emits a fluorescence 9 and the fluorescence 9 is photographed into an imaging device 2 as shown in FIGS. 1 and 3. Further, noise light 10a emitted from a surface site 12a on the imaging object 13 is also photographed into the imaging device 2 at the same time.

At STEP 2, an image A obtained by being photographed into the imaging device 2 is stored in a recorder. Sites where the intensity of visible light is high in the image A are the site of the fluorescence 9 (site of the leakage oil 11) and the surface site 12a.

At STEP 3, the light source 1a is switched off.

At STEP 4, the imaging object 13 is irradiated by a second ultraviolet light source 1b. When the ultraviolet light component 7b of the irradiated light is emitted to the leakage oil 11, the leakage oil 11 emits a fluorescence 9 and the fluorescence 9 is photographed into the imaging device 2 as shown FIGS. 1 and 4. Further, noise light 10b emitted from a surface site 12b on the imaging object 13 is also photographed into the imaging device 2 at the same time.

At STEP 5, an image B obtained by being photographed into the imaging device 2 is stored in the recorder. Sites where the intensity of visible light is high in the image B are the site of the fluorescence 9 (site of the leakage oil 11) and the surface site 12b.

At STEP 6, the light source 1b is switched off.

At STEP 7, the images A and B photographed at STEP 2 and STEP 5 are displayed on a display 5 at the same time. The site of the leakage oil 11 where the fluorescence 9 is generated emits light at the same position in both the images and hence is judged as a leakage oil (AND condition). In contrast, since the surface site 12a and the surface site 12b emit light at different positions in the respective images, an operator displays the situation of the light emission on a display, confirms the situation visually, and judges the sites as noise light emitting sites (OR condition). In this way, the leakage oil 11 can easily be detected and identified visually regardless of the skills of an operator.

Second Embodiment

Figure 5:
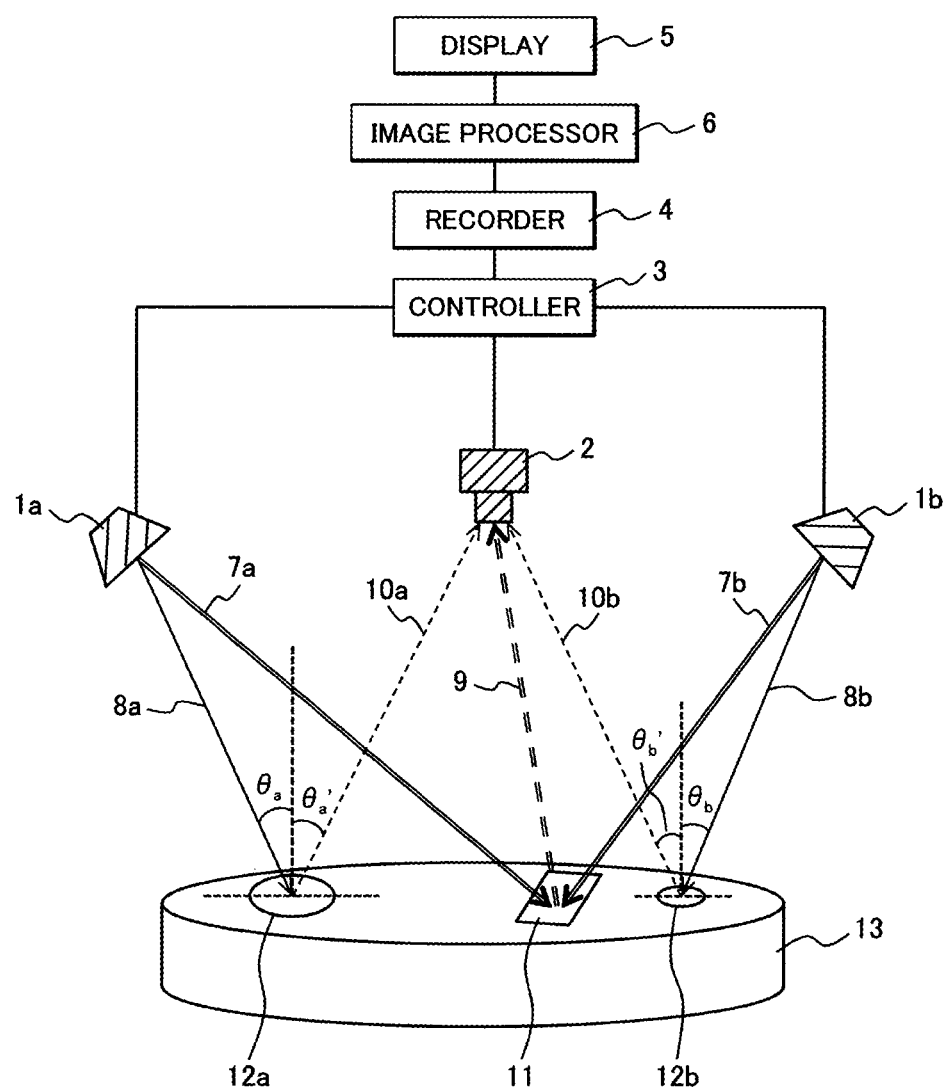
FIG. 5 is a view showing a second embodiment of a method and a system for detecting leakage oil according to the present invention.

FIG. 5 is a view showing a second embodiment of a method and a system for detecting leakage oil according to the present invention. Here, a component identical to the first embodiment is represented by an identical reference sign, the explanations are omitted, and only different parts are explained. At an image processor 6, an image recorded in a recorder 4 called up and a leakage oil 11 is judged automatically. A judgment result is displayed on a display 5.

Figure 6:
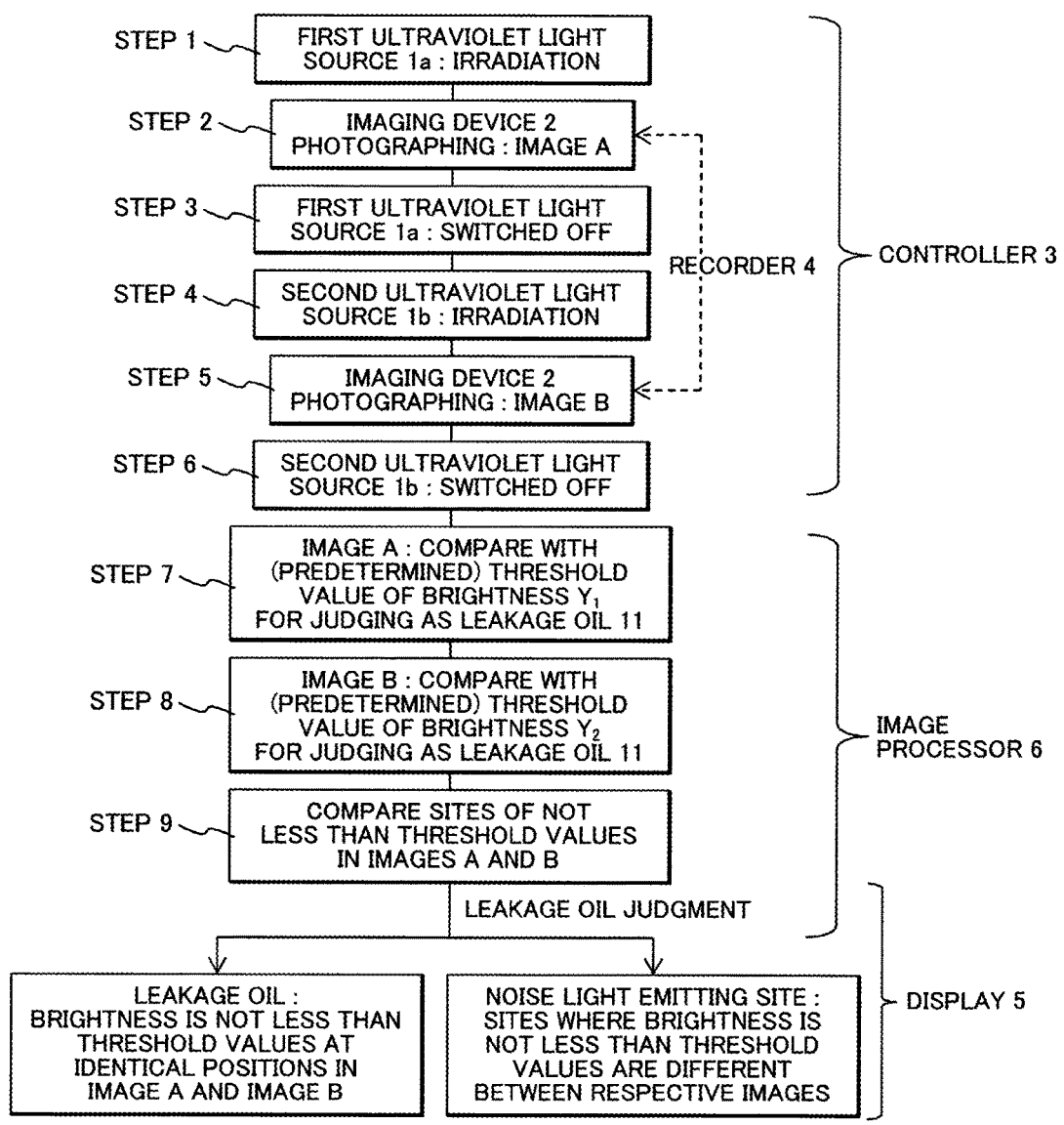
FIG. 6 is a flowchart explaining leakage oil detection operation in the second embodiment.

FIG. 6 is a flowchart in the case of automatically detecting a leakage oil 11 by a method and a system for detecting leakage oil according to the second embodiment. Here, the operations at STEP 1 to STEP 6 are identical to the first embodiment.

At STEP 7, a photographed image A is called up, R, G, and B values of each pixel are extracted, and a brightness $Y_n$ is computed. An example of a mathematical expression representing $Y_n$ is $Y_n=0.299R+0.587G+0.114B$ (1), which is generally known. Here, n is distinguished as n=1 at STEP 7 and n=2 at STEP 8 described below.

A brightness $Y_1$ of the image A is compared with a predetermined threshold value of brightness for judging as a leakage oil 11 at the image processor 6 and a site of not less than the threshold value is recorded.

At STEP 8, a brightness of each pixel in an image B is computed by using the mathematical expression (1). Successively, in the same way as STEP 7, the brightness is compared with a predetermined threshold value of brightness for judging as a leakage oil 11 at the image processor 6 and a site of not less than the threshold value is recorded.

Here, the threshold values of brightness in the respective images A and B may be: measured and evaluated beforehand by using a first ultraviolet light source 1a and a second ultraviolet light source 1b in the state of not having a leakage oil 11 such as the state of newly installing a transformer or the like and in the state of artificially attaching oil; and set as back data in the image processor 6.

At STEP 9, the sites of not less than the threshold values of brightness respectively in the image A and the image B are compared. When a site where a brightness $Y_1$ is not less than the threshold value of brightness in the image A and a site where a brightness $Y_2$ is not less than the threshold value of brightness in the image B coincide with each other, the sites are judged as a leakage oil 11. When a site where a brightness $Y_1$ is not less than the threshold value of brightness in the image A and a site where a brightness $Y_2$ is not less than the threshold value of brightness in the image B are different from each other, the sites are judged as the sites emitting noise light 10a and 10b.

As stated above, in the present embodiment, by using threshold values of brightness, it is possible to judge leakage oil automatically and improve detection accuracy at the same time.

Third Embodiment

Figure 7:
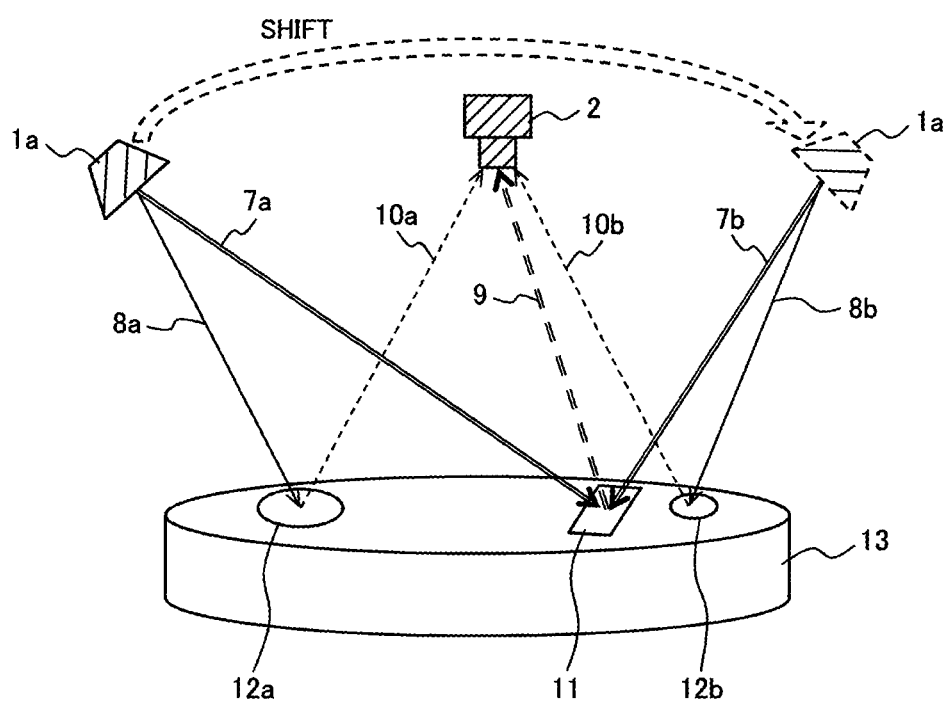
FIG. 7 is a view showing a third embodiment of a method and a system for detecting leakage oil according to the present invention.

FIG. 7 is a view showing a third embodiment of a method and a system for detecting leakage oil according to the present invention. A controller 3, a recorder 4, and a display 5 are identical to the first and second embodiments and an image processor 6 identical to the second embodiment and hence they are omitted.

Although sites emitting a fluorescence 9 and noise light 10a and 10b are detected and identified by arranging a first ultraviolet light source 1a and a second ultraviolet light source 1b in each of the first and second embodiments, in the present embodiment, only a first ultraviolet light source 1a is arranged and is shifted to a position where a second ultraviolet light source 1b is arranged as explained in the first and second embodiments by a light source shifting means arranged in the vicinity of a transformer. The configurations other than the above configurations are identical to the first and second embodiments. Here, as the light source shifting means, a rail, a robot arm, or the like is appropriate but the light source shifting means is not limited to the means.

Figure 8:
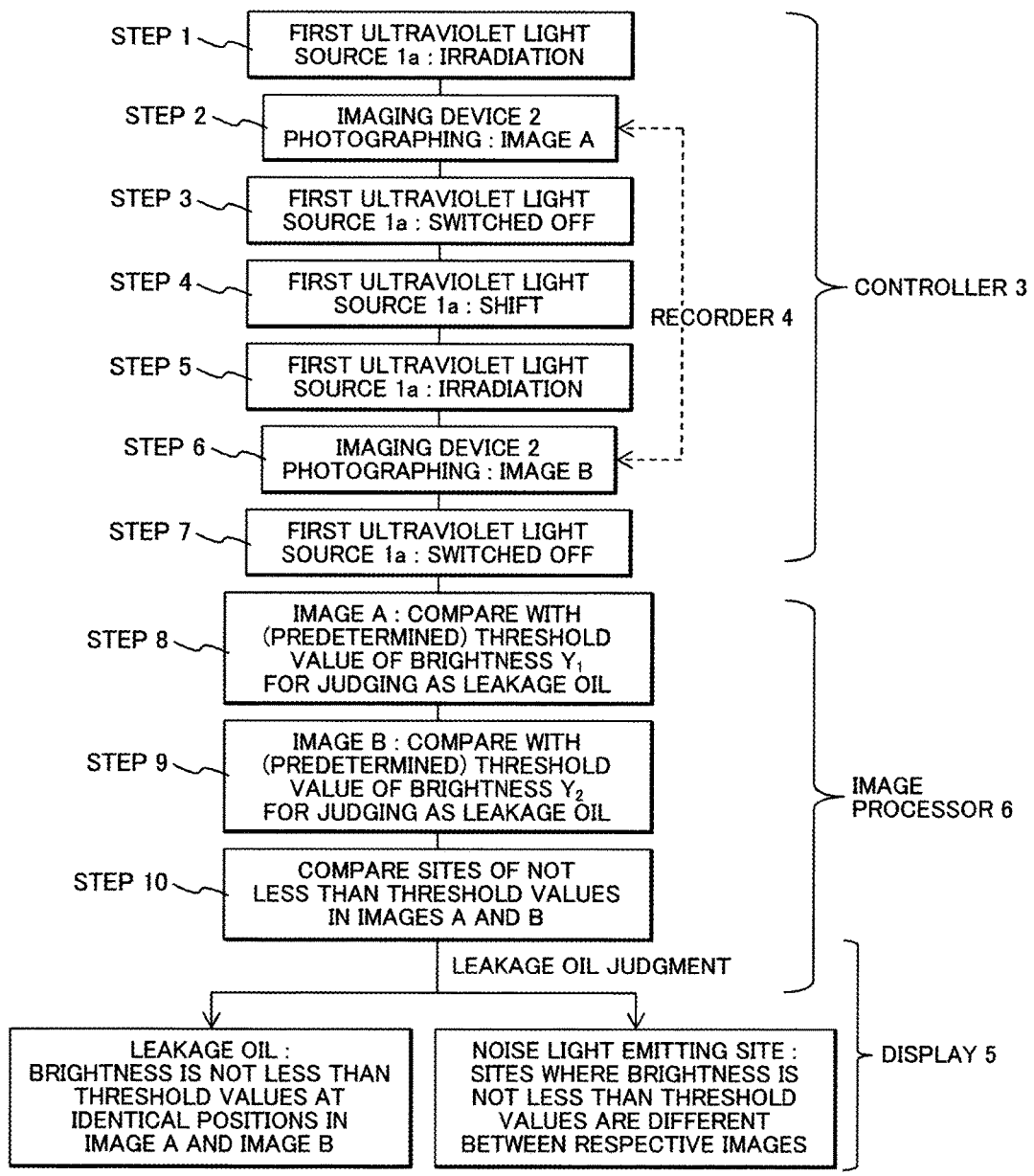
FIG. 8 is a flowchart explaining leakage oil detection operation in the third embodiment.

FIG. 8 is a flowchart in the case of automatically detecting leakage oil by a method and a system for detecting leakage oil according to the third embodiment. Here, additional items in the present embodiment are explained in contrast with FIG. 6.

The steps other than STEP 4 in FIG. 8 are identical to the second embodiment. At STEP 4 in FIG. 8, a first ultraviolet light source 1a is shifted by the method described above after the photographing of an image A is completed at STEP 3 in FIG. 8.

Figure 2:
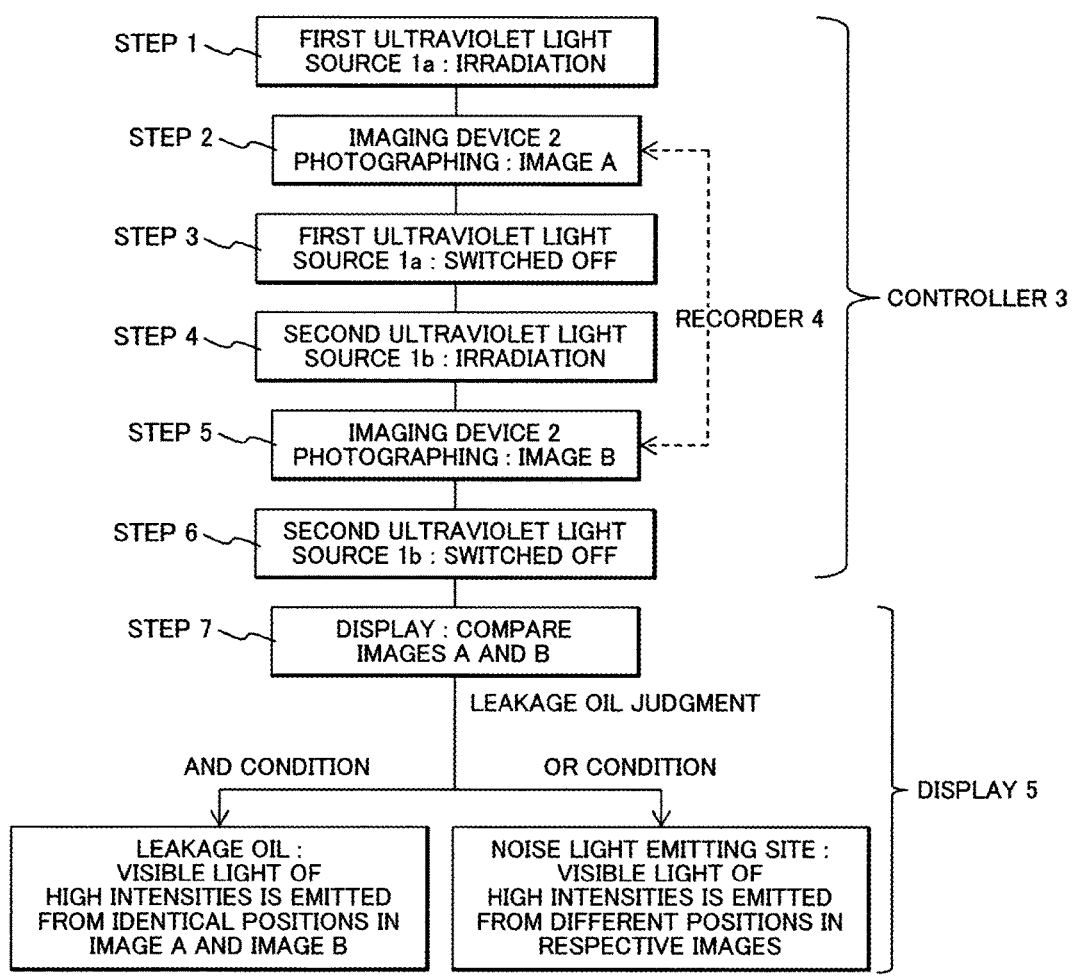
FIG. 2 is a flowchart explaining leakage oil detection operation in the first embodiment.

Meanwhile, although the flowchart of the third embodiment is shown as an example here, in the flowchart of the first embodiment shown in FIG. 2, only one ultraviolet light source may be used by adding STEP 4 shown in FIG. 8 of the present embodiment between STEP 3 and STEP 4 in FIG. 2.

Fourth Embodiment

Figure 9:
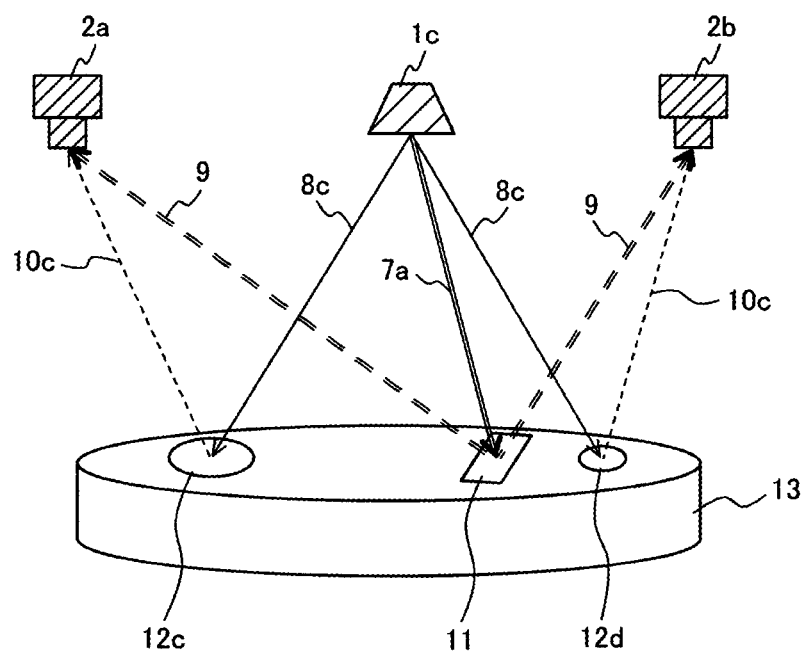
FIG. 9 is a view showing a fourth embodiment of a method and a system for detecting leakage oil according to the present invention.

FIG. 9 is a view showing a fourth embodiment of a method and a system for detecting leakage oil according to the present invention. A controller 3, a recorder 4, and a display 5 are identical to the first and second embodiments and an image processor 6 is identical to the second embodiment and hence they are omitted. Here, a constituent component identical to the above embodiments is represented by an identical reference sign, the explanations are omitted, and only different parts are explained.

In the present embodiment, only an ultraviolet light source 1c is arranged and imaging devices 2a and 2b are arranged. At a surface site 12c of an imaging object 13, noise light 10c caused by a visible light component 8c of irradiation light emitted from the ultraviolet light source 1c is photographed into the imaging device 2a but is not photographed into the imaging device 2b. Likewise, at a surface site 12d, noise light 10c caused by the visible light component 8c is not photographed into the imaging device 2a but is photographed into the imaging device 2b.

Figure 10:
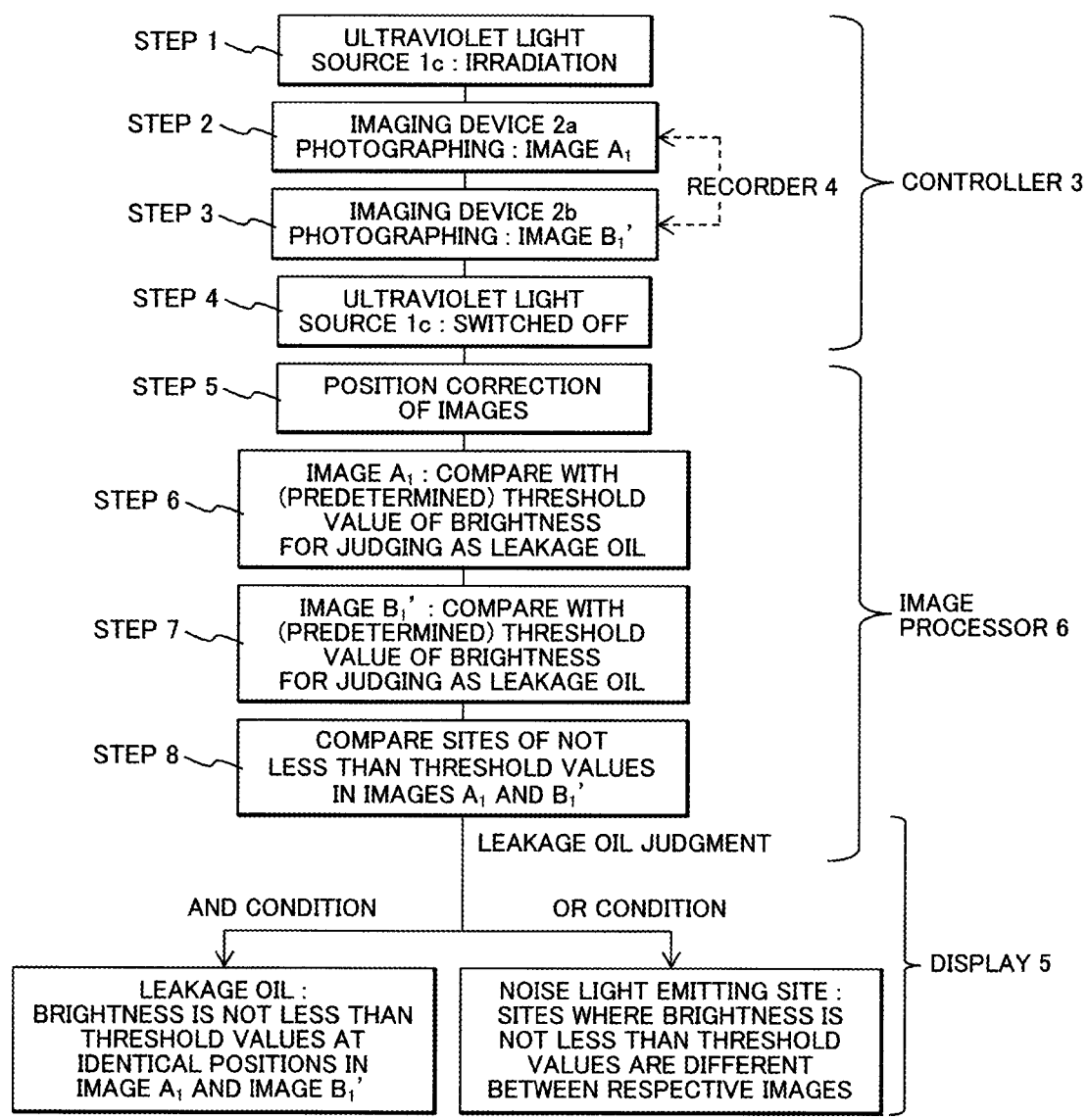
FIG. 10 is a flowchart explaining leakage oil detection operation in the fourth embodiment.

FIG. 10 is a flowchart in the case of automatically detecting a leakage oil 11 by a method and a system for detection according to the fourth embodiment.

At STEP 1, an imaging object 13 is irradiated by an ultraviolet light source 1c.

At STEP 2, an image $A_1$ obtained by being photographed with an imaging device 2a is stored in a recorder 4. In the image $A_1$, the sites showing visible light of high intensities come to be the site of a leakage oil 11 and a surface site 12c.

At STEP 3, an image $B_1$ obtained by being photographed with an imaging device 2b is stored in the recorder 4. In the image $B_1$, the sites showing visible light of high intensities come to be the site of the leakage oil 11 and a surface site 12d.

At STEP 4, the ultraviolet light source 1c is switched off.

At STEP 5, the images $A_1$ and $B_1$ are read out from the recorder 4 and processed at an image processor 6. The two imaging devices 2a and 2b photograph the imaging object 13 from different places and hence the positions of the images are corrected so that the positions of the imaging object 13 may take identical positions in the images $A_1$ and $B_1$.

Meanwhile, it is preferable, for example, to obtain a correction coefficient beforehand by using a plurality of characteristic spots as landmarks on an imaging object 13 so as to be able to correct an image position easily. Otherwise, by arranging imaging devices 2a and 2b so as to be equally distant from the surface of an imaging object 13 and parallel with the surface of the imaging object 13, a position can be corrected more easily. That is, multiple corrections such as magnification and minification of an image come to be unnecessary by such an arrangement.

An image $B_1'$ obtained by correcting the image $B_1$ and the image $A_1$ are stored in the image processor 6.

At STEP 6 to STEP 8, leakage oil is judged automatically by using $A_1$ and $B_1'$. The automatic judgment method is identical to the second embodiment and hence the explanations are omitted.

Fifth Embodiment

Figure 11:
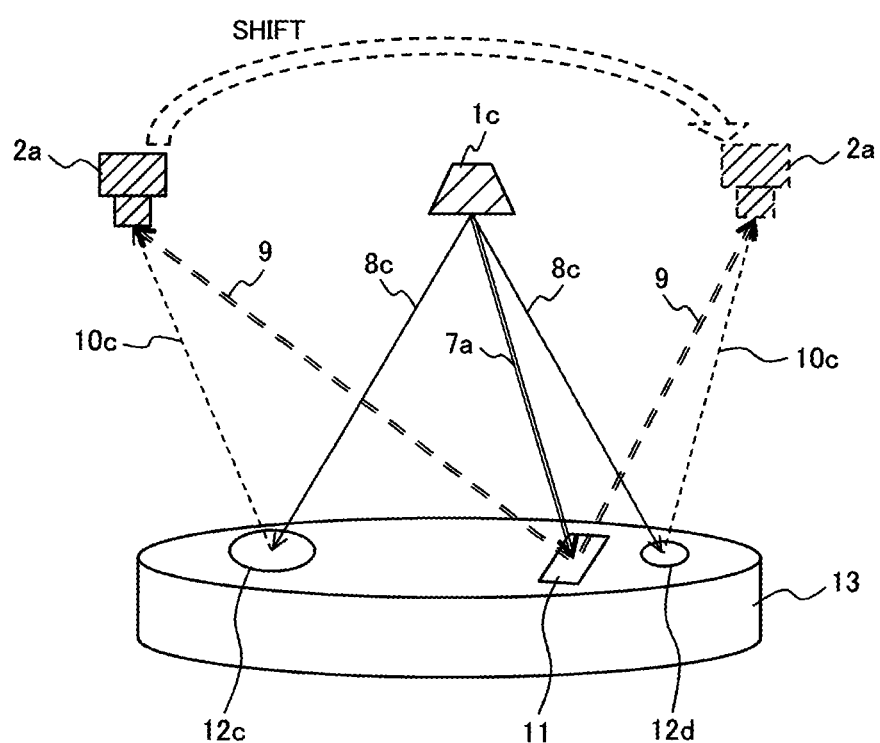
FIG. 11 is a view showing a fifth embodiment of a method and a system for detecting leakage oil according to the present invention.

FIG. 11 is a view showing a fifth embodiment of a method and a system for detecting leakage oil according to the present invention. A controller 3, a recorder 4, and a display 5 are identical to the first and second embodiments and an image processor 6 is identical to the second embodiment and hence they are omitted. Here, a constituent component identical to the fourth embodiment is represented by an identical reference sign, the explanations are omitted, and only different parts are explained.

Although imaging devices 2a and 2b are installed in the fourth embodiment, only an imaging device 2a is installed in the present embodiment. The imaging device 2a is shifted to a position where an imaging device 2b is installed in the fourth embodiment by a shifting means of the imaging device 2a arranged in the vicinity of a transformer. Meanwhile, as the shifting means of an imaging device, a rail or a robot arm is preferably used in the same way as the third embodiment but the shifting means of an imaging device is not limited to the means.

Figure 12:
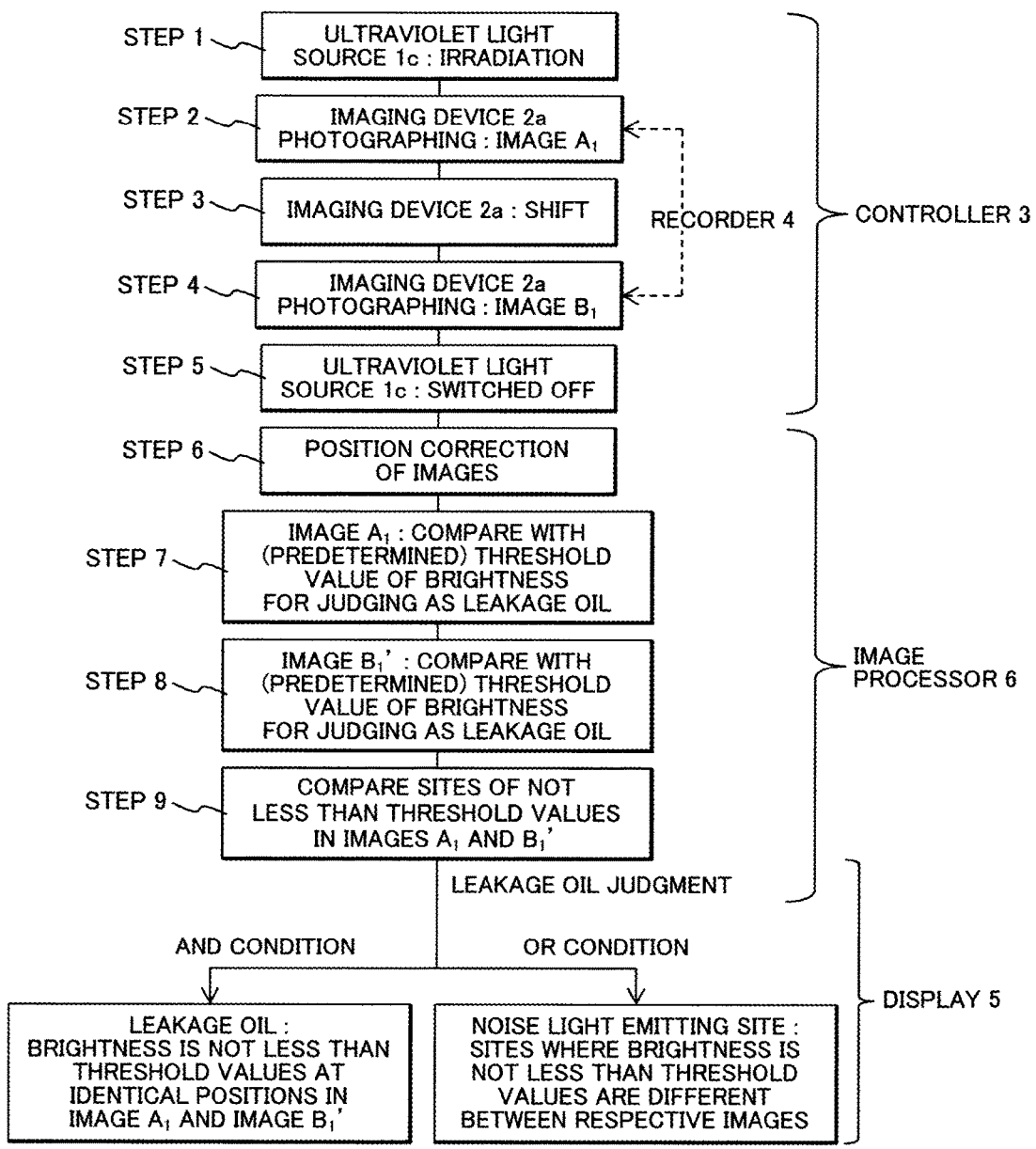
FIG. 12 is a flowchart explaining leakage oil detection operation in the fifth embodiment.

FIG. 12 is a flowchart in the case of automatically detecting a leakage oil 11 by a method and a system for detecting leakage oil according to the fifth embodiment. The steps other than STEP 3 are identical to the fourth embodiment and hence the explanations are omitted. At STEP 3, the imaging device 2a is shifted by the method described above after the photographing of an image $A_1$ is completed at STEP 2.

Sixth Embodiment

Figure 13:
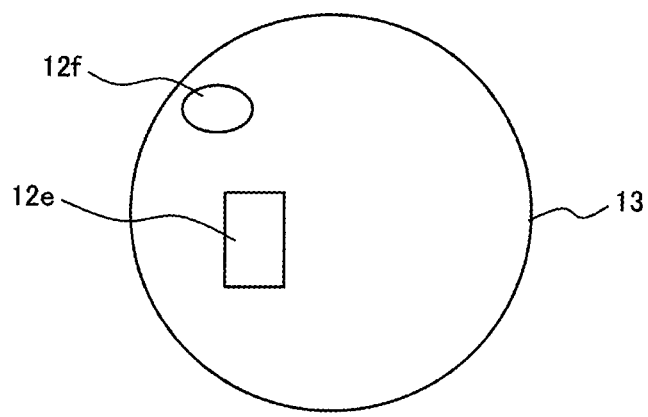
FIG. 13 is a schematic view showing an image photographed in a sixth embodiment of a method and a system for detecting leakage oil according to the present invention.
Figure 14:
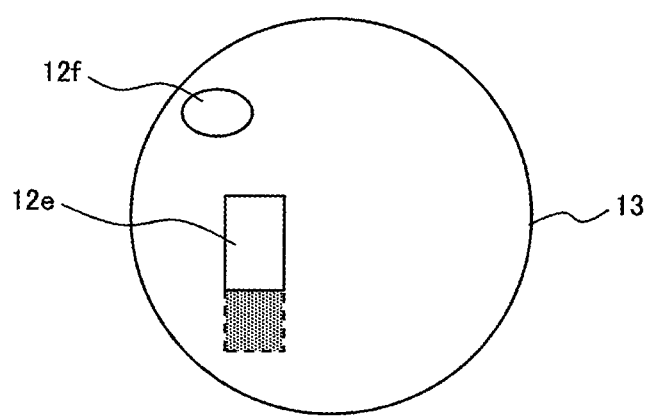
FIG. 14 is a schematic view showing an image photographed after a predetermined time interval in the sixth embodiment of a method and a system for detecting leakage oil according to the present invention.

The present embodiment is a method of detecting oil attaching to a side face of a transformer by: using a first ultraviolet light source 1a and an imaging device 2, those being fixed; photographing an imaging object 13 at a predetermined time interval; detecting change of the shape of a leakage oil 11 in obtained images; and identifying the leakage oil 11 and a site emitting noise light 10a. FIGS. 13 and 14 are schematic views showing two images photographed at a predetermined time interval.

The sites emitting visible light of high intensities in an imaging object 13 in FIG. 13 are a site 12e (referred to as a leakage oil site) and a site 12f (referred to as a site emitting noise light). The shape of a leakage oil 11 changes with the lapse of time by the influence of gravity. FIG. 14 is a schematic view of an image of the imaging object 13 photographed after a predetermined time interval. The leakage oil 11 flows downward through a side face of a device and hence the shape changes as shown by the broken line. On the other hand, the site 12f is the site emitting the noise light 10a and hence the shape does not change regardless of the lapse of time. By comparing the images, it is possible to detect and identify: the site 12f where the emission shape does not change as a site emitting the noise light 10a; and the site where the emission shape changes as the site of the leakage oil 11.

Figure 15:
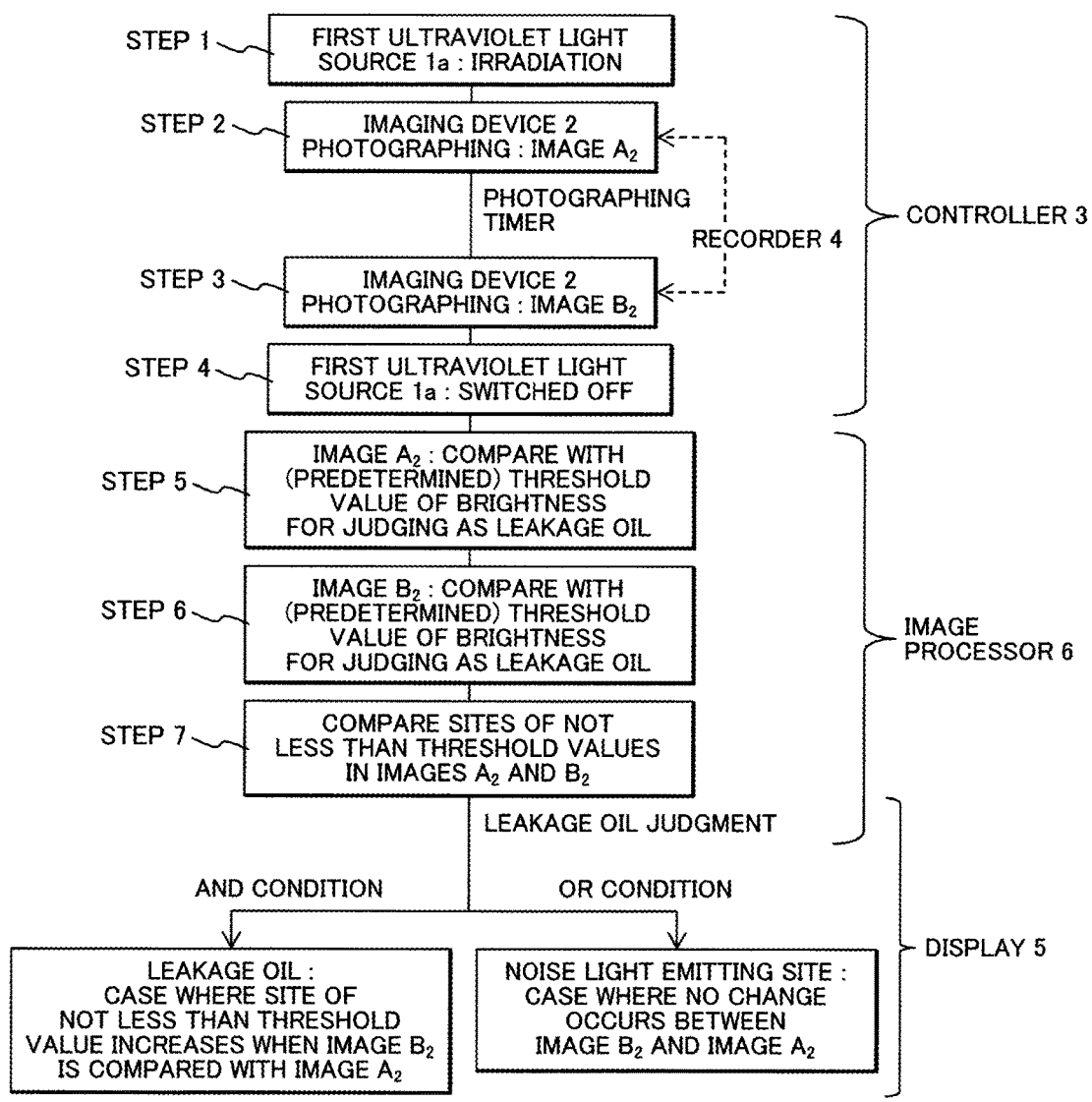
FIG. 15 is a flowchart explaining leakage oil detection operation in the sixth embodiment.

FIG. 15 is a flowchart in the case of automatically detecting leakage oil by a method and a system for detection according to the fifth embodiment. At STEP 1, an imaging object 13 is irradiated by a first ultraviolet light source 1a.

At STEP 2, an image $A_2$ obtained by being photographed with an imaging device 2 is stored in a recorder 4. Sites emitting visible light of high intensities on the surface of an imaging object 13 in the image $A_2$ are a surface site 12e of a leakage oil 11 and a surface site 12f.

At STEP 3, an image $B_2$ obtained by being photographed again with the imaging device 2 after a predetermined time interval is stored in the recorder 4. Sites emitting visible light of high intensities in the image $B_2$ are the surface site 12e of the leakage oil 11 and the surface site 12f.

At STEP 4, the first ultraviolet light source 1a is switched off. STEP 5 and STEP 6 are identical to the second embodiment and hence the explanations are omitted.

At STEP 7, the sites of not less than threshold values of brightness in the images $A_2$ and $B_2$ are compared. When the site of not less than a threshold value of brightness increases and the shape of the site changes in $B_2$ in comparison with $A_2$, the site is judged as a leakage oil 11. On the other hand, when the site does not change, the site is judged as a site emitting noise light 10a.

Seventh Embodiment

Figure 16:
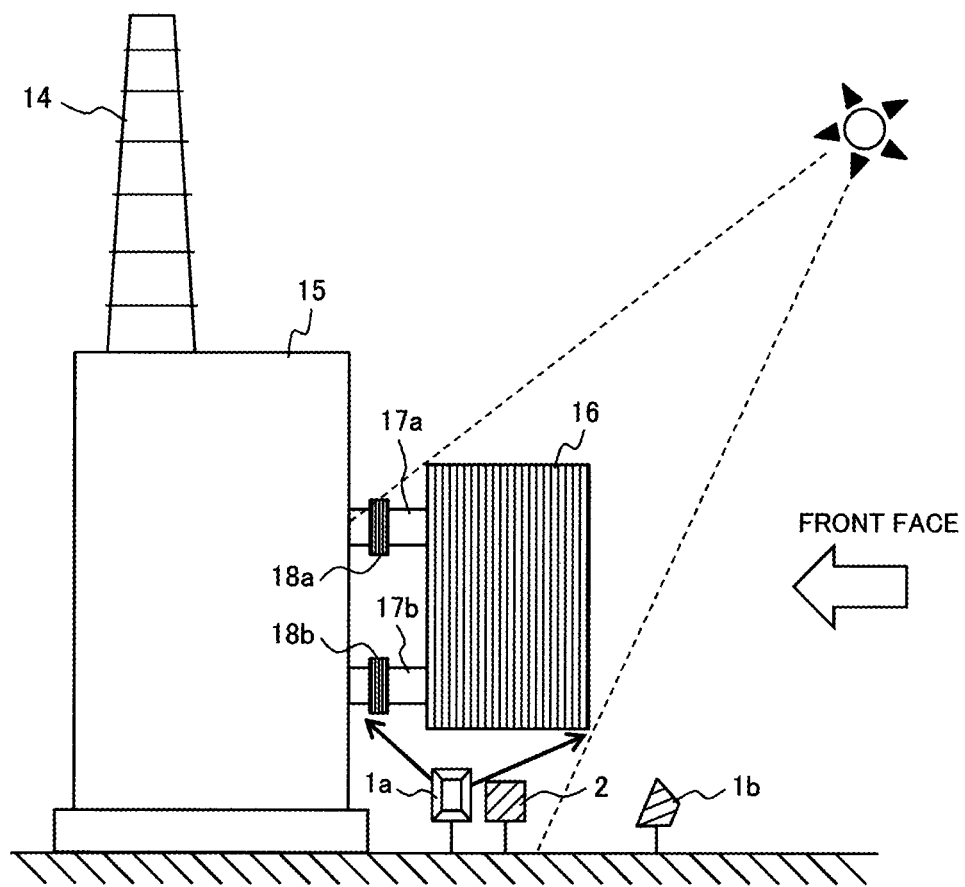
FIG. 16 is a view showing a seventh embodiment of a method and a system for detecting leakage oil according to the present invention.

The present embodiment shows a method and a system for detecting a leakage oil 11 at a radiator 16 and a junction 18b of a lower pipe on the basis of an example of an oil-filled transformer having a bushing 14, a tank 15, the radiator 16, an upper pipe 17a and a lower pipe 17b connecting the tank 15 to the radiator 16, a junction 18a of the upper pipe, and the junction 18b of the lower pipe and being generally used in a power system as shown in FIG. 16.

An oil-filled transformer has a structure formed by, as the name suggests, filling a bushing 14, a tank 15, a radiator 16, an upper pipe 17a, and a lower pipe 17b with an insulation oil and junctions 18a and 18b of the upper and lower pipes are fixed generally with bolts and nuts with packings interposed.

FIG. 16 is a side view in the state of arranging a first ultraviolet light source 1a, a second ultraviolet light source 1b, and an imaging device 2 around the transformer.

Figure 17:
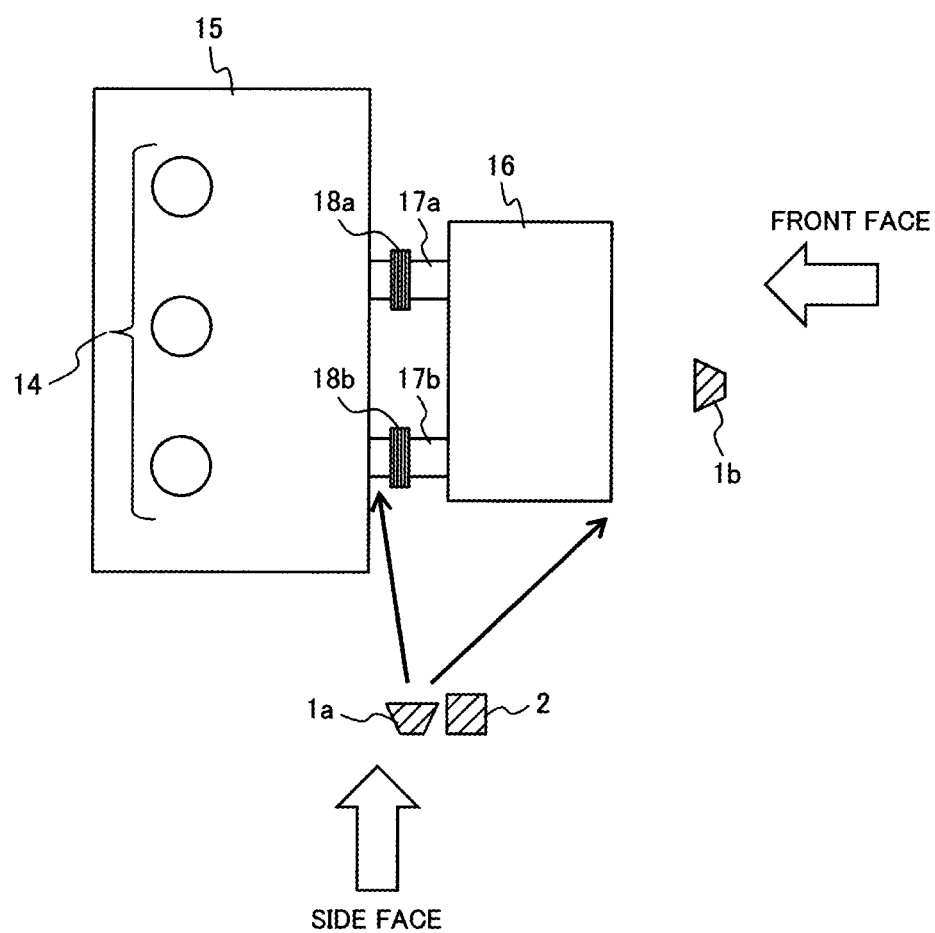
FIG. 17 is a top view of FIG. 16.

FIG. 17 is a top view of FIG. 16. The first ultraviolet light source 1a and the imaging device 2 are arranged at places apart from the side face of the radiator 16. Further, the second ultraviolet light source 1b is arranged at a place apart from the front face of the radiator 16.

The first ultraviolet light source 1a, the second ultraviolet light source 1b, and the imaging device 2 are installed so as to be lower than the height of the bottom face of the radiator 16 and at places and heights allowing the lower part of the radiator 16 and the bottom part of the junction 18b of the lower pipe to be irradiated.

By such arrangement, a leakage oil 11 can be detected at the sites of the radiator 16 and the junction 18b of the lower pipe irradiated by the first ultraviolet light source 1a and the second ultraviolet light source 1b with the configuration of two ultraviolet light sources 1a and 1b and one imaging device 2. The details of the method and system for detecting the leakage oil 11 are the same as those explained in the second embodiment and hence the explanations are omitted. Meanwhile, as a result of earnest studies by the present inventors, the detection sensitivity of leakage oil can be increased when a luminance in the surrounding environment of a leakage oil detector system is 50 lx or lower. By detecting leakage oil by making use of the shadow of a transformer or after-sunset, in particular night time, therefore, detection sensitivity can be increased.

Further, costs for introducing such a detector system can be reduced by using a monitoring camera in a transformer station as an imaging device 2 or using an existing power source feeding electricity to an infrared sensor for monitoring for example in a premise where a leakage oil detector system is installed. Here, the power source of the detector system is not limited to the case and a battery or the like may be used.

REFERENCE SIGNS LIST

100 Leakage oil detector system
1a First ultraviolet light source
1b Second ultraviolet light source
1c Ultraviolet light source
2 Imaging device
2a Imaging device
2b Imaging device
3 Controller
4 Recorder
5 Display
6 Image processor
7a Ultraviolet light component in irradiation light of first ultraviolet light source 1a emitted to leakage oil
7b Ultraviolet light component in irradiation light of second ultraviolet light source 1b emitted to leakage oil
8a Visible light component in irradiation light of first ultraviolet light source 1a
8b Visible light component in irradiation light of second ultraviolet light source 1b
8c Visible light component in irradiation light of ultraviolet light source 1c
9 Fluorescence
10a Specular reflected light (noise light) of visible light component in irradiation light of first ultraviolet light source 1a
10b Specular reflected light (noise light) of visible light component in irradiation light of second ultraviolet light source 1b
10c Specular reflected light (noise light) of visible light component in irradiation light of ultraviolet light source 1c
11 Leakage oil
12a Surface site of imaging object 13
12b Surface site of imaging object 13
12c Surface site of imaging object 13
12d Surface site of imaging object 13
12e Surface site of imaging object 13
12f Surface site of imaging object 13
13 Imaging object
14 Transformer bushing
15 Transformer tank
16 Transformer radiator
17a Upper pipe connecting transformer tank and radiator
17b Lower pipe connecting transformer tank and radiator
18a Junction of upper pipe
18b Junction of lower pipe

The invention claimed is:

1. A leakage oil detector system having:
an ultraviolet light source that is arranged so as to irradiate an oil-filled device from a plurality of different incidence angles, is switched on and off at the respective incidence angles in sequence, and includes a wavelength exciting oil;
an imaging device to photograph said oil-filled device irradiated with ultraviolet light emitted from the ultraviolet light source when the ultraviolet light source is switched on;
a recorder to record respective images photographed by the imaging device;
an image processor to compare the respective images, judge a site where a light emitting position does not change always as a leakage oil site, and judge a site emitting light or not emitting light at different positions as a noise light site; and
a display to display the respective images.

2. A leakage oil detector system according to claim 1, wherein the ultraviolet light source including the wavelength exciting oil has a light emission peak of 265±50 nm, 275±50 nm, 345±50 nm, or 365±50 nm.

3. A leakage oil detector system according to claim 1, wherein the image processor quantitatively judges light quantities of the leakage oil site and the noise light site.

4. A leakage oil detector system according to claim 3, wherein the leakage oil detector system has a judging function of a threshold value of brightness in order to quantitatively judge the light quantity at the image processor.

5. A leakage oil detector system according to claim 4, wherein the judging function has the light quantity in the state of no leakage oil as back data beforehand.

6. A leakage oil detector system according to claim 1, wherein the ultraviolet light source has a shifting means.

7. A leakage oil detector system according to claim 1, wherein the leakage oil detector system further has a position correction means to positionally correct the respective images.

8. A leakage oil detection method including the steps of:
arranging an ultraviolet light source including a wavelength exciting oil so as to irradiate an oil-filled device from a plurality of different incidence angles;
switching the ultraviolet light source on and off at the respective incidence angles in sequence;
photographing the oil-filled device irradiated with ultraviolet light emitted from the ultraviolet light source when the ultraviolet light source is switched on; and
comparing the respective photographed images, judging a site where a light emitting position does not change always as a leakage oil site, and judging a site emitting light or not emitting light at different positions as a noise light site.

9. A leakage oil detection method according to claim 8, wherein the ultraviolet light source including the wavelength exciting oil has a light emission peak of $265\pm50$ nm, $275\pm50$ nm, $345\pm50$ nm, or $365\pm50$ nm.

* * * * *